United States Patent
Koftis et al.

(10) Patent No.: US 8,575,343 B2
(45) Date of Patent: Nov. 5, 2013

(54) PROCESS FOR THE PREPARATION OF A PROPENAL INTERMEDIATE AND DERIVATIVES THEREOF

(75) Inventors: Theoharis V. Koftis, Salonika (GR); Thanos Andreou, Salonika (GR); Aristotelis Menisiou, Salonika (GR); Efstratios Neokosmidis, Salonika (GR); Asteria Zitrou, Salonika (GR)

(73) Assignee: Pharmathen S.A., Pallini, Attikis (GR)

( * ) Notice: Subject to any disclaimer, the term of this patent is extended or adjusted under 35 U.S.C. 154(b) by 0 days.

(21) Appl. No.: 13/699,569

(22) PCT Filed: Jun. 7, 2010

(86) PCT No.: PCT/EP2010/003398
§ 371 (c)(1),
(2), (4) Date: Nov. 21, 2012

(87) PCT Pub. No.: WO2011/154015
PCT Pub. Date: Dec. 15, 2011

(65) Prior Publication Data
US 2013/0066074 A1    Mar. 14, 2013

(51) Int. Cl.
*C07D 239/02* (2006.01)

(52) U.S. Cl.
USPC .......................................................... 544/297

(58) Field of Classification Search
None
See application file for complete search history.

(56) References Cited

FOREIGN PATENT DOCUMENTS

| WO | 2006100698 A1 | 9/2006 |
|---|---|---|
| WO | 2008072078 A1 | 6/2008 |
| WO | WO 2008112317 A2 * | 9/2008 |

* cited by examiner

*Primary Examiner* — Andrew D Kosar
*Assistant Examiner* — John S Kenyon
(74) *Attorney, Agent, or Firm* — AKC Patents LLC; Aliki K. Collins

(57) ABSTRACT

The present invention provides an improved process for the preparation of (E)-N-(4-(4-fluorophenyl)-6-isopropyl-5-(3-oxoprop-1-enyl)pyrimidin-2-yl)-N-methyl methanesulfonamide, which is a useful intermediate for the preparation of (3R,5S,E)-7-(4-(4-fluorophenyl)-6-isopropyl-2-(N-methyl methylsulfonamido)pyrimidin-5-yl)-3,5-dihydroxy hept-6-enoic acid, commonly known as Rosuvastatin.

15 Claims, No Drawings

PROCESS FOR THE PREPARATION OF A PROPENAL INTERMEDIATE AND DERIVATIVES THEREOF

TECHNICAL FIELD OF THE INVENTION

The present invention relates to an improved process for the preparation of propenal intermediate and derivatives thereof and in particular to a process for the preparation of (E)-N-(4-(4-fluorophenyl)-6-isopropyl-5-(3-oxoprop-1-enyl)pyrimidin-2-yl)-N-methylmethanesulfonamide, and the use thereof as an intermediate in the process for large scale production of Rosuvastatin.

BACKGROUND OF THE INVENTION

Rosuvastatin belongs to a class of drugs called statins, which act as inhibitors of 3-hydroxy-3-methylglutaryl-coenzyme-A (HMG-CoA) reductase. Statins are effective in reducing low-density lipoprotein (LDL) particles concentration in the blood stream and used in the treatment of hypercholesterolemia and hyperlipoproteinemia. Moreover, they are very useful in preventing coronary heart disease (CHD), which continues to be a major health problem in developed countries.

Rosuvastatin is used in the form of Rosuvastatin calcium, which is more desirable since it can be more efficiently formulated. This is important, because formulations need to meet certain pharmaceutical requirements and specifications. Rosuvastatin calcium can be easily formulated in the form of tablets, capsules, lozenges, powders, and other forms for oral administration.

Rosuvastatin calcium is chemically designated as (3R,5S,E)-7-(4-(4-fluorophenyl)-6-isopropyl-2-(N-methyl methylsulfonamido)pyrimidin-5-yl)-3,5-dihydroxyhept-6-enoic acid calcium salt (2:1). Rosuvastatin calcium is represented by the following structure of formula II:

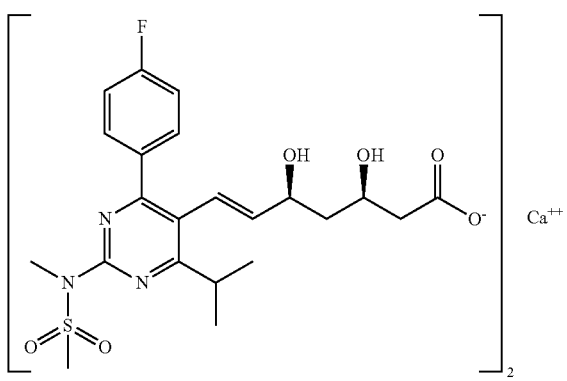

(E)-N-(4-(4-fluorophenyl)-6-isopropyl-5-(3-oxoprop-1-enyl)pyrimidin-2-yl)-N-methylmethanesulfonamide is also known as (2E)-3-[4-(4-fluorophenyl)-6-isopropyl-2-(N-methylsulfonylamino)pyrimidin-5-yl]-propenal and has the following structural formula (I). Said compound of formula (I) is a useful intermediate for the preparation of Rosuvastatin.

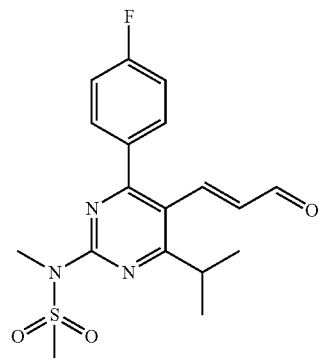

Various methods are already known for the preparation of (E)-N-(4-(4-fluorophenyl)-6-isopropyl-5-(3-oxoprop-1-enyl)pyrimidin-2-yl)-N-methylmethanesulfonamide or derivates thereof. Prior art processes for the preparation of compound of Formula (I) present the disadvantage of non-satisfactory yield of the product. Furthermore, the compound often comprises significant amounts of impurities.

WO-A-2006/100689 discloses a process for the preparation of the propenal intermediate, wherein the starting material N-(4-(4-fluorophenyl)-5-formyl-6-isopropylpyrimidin-2-yl)-N-methylmethanesulfonamide, herein referred to as the carboxaldehyde intermediate, is subjected to a Wittig-type coupling reaction with a stabilized phosphorus species. The propenal intermediate is further prepared by reduction using DIBAL then oxidation using pyridine/$CrO_3$.

However, this process requires the use of $CrO_3$ in large excess, which is a known toxic, corrosive and carcinogenic reagent. Further, the addition and quenching of the DIBAL reagent must be carried out with extreme caution, strictly at low temperatures for safety reasons.

Moreover, this process requires the use of column chromatography for the isolation of the Witting-coupling product, which results in a process that is not cost effective for large-scale industrial production. The total reaction time of the process is more than 15 hours, wherein 6 hours out of said total reaction time are under reflux conditions, and additional time must be invested in the lengthy workup procedures of the last two steps.

WO-A-2008/072078 discloses a four-step process for the preparation of the propenal intermediate from the carboxaldehyde intermediate. This process requires a lengthy basic hydrolysis step to generate a mixed anhydride intermediate. This intermediate is then reduced to the corresponding alcohol intermediate, which is further oxidized to obtain the carboxaldehyde intermediate. The reaction step requires either cryogenic conditions using a highly reactive and hazardous $LiAlH_4$ reagent or long reaction time and column purification using $NaBH_4$.

Further, in the final oxidation step, $MnO_2$ is added in large excess. The total reaction time is too long and the yield of said process is low. This process is not feasible for large scale production.

WO-A-2010/038124 discloses a two-step process for the preparation of the propenal intermediate, comprising a first step of a high-yielding Grignard reaction, which leads to a secondary alcohol intermediate, and a second step such as a chain extension process using a highly toxic and corrosive $POCl_3$ reagent in molar excess. The target propenal intermediate is purified by recrystallization. The total reaction time of this process exceeds 36 hours and the overall yield is moderate.

Although each of the above patents represents an attempt to overcome the use of costly and hazardous material, there still exists a need for a cost-effective and safer process for large scale production which provides higher yield with higher purity.

SUMMARY OF THE INVENTION

It is, therefore, an object of the present invention to provide an improved process for the preparation of the propenal intermediate of formula I or its derivatives, which overcomes the deficiencies of the prior art processes and results to a cost effective industrial production without sacrificing the yield and quality of the product.

Another object of the present invention is to provide an improved method for the preparation of the propenal intermediate of formula I or its derivatives by selecting the appropriate reactants, catalysts, solvent systems and conditions used during the organic reactions, so that the purity and yield of the reaction are increased.

Further object of the present invention is to provide an improved less time-consuming process for the preparation of propenal intermediate of formula I or its derivatives, by using milder and safer reaction conditions and by minimizing the presence of any contaminants and formed by-products during the reactions.

In accordance with the above objects of the present invention, a process for the preparation of propenal intermediate of formula I or its derivatives is provided comprising the following steps:

a) Treatment of N-(4-(4-fluorophenyl)-5-formyl-6-isopropylpyrimidin-2-yl)-N-methyl methanesulfonamide of formula III:

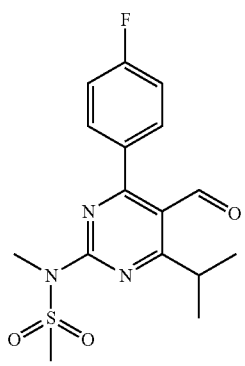

III with a compound selected from
i) an unsaturated compound of formula IV

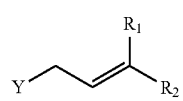

IV wherein $R_1$ and $R_2$ are independently selected from H, alkyl, aryl or a heterocyclic moiety;
Y is selected from M, MX, $BR_aR_b$ and $MR_aR_bR_c$, wherein M is selected from alkali, Zn, Mg, Sn and Si;
X is selected from Cl, Br and I;
$R_a$, $R_b$ and $R_c$ are independently selected from X, H, $C_1$-$C_2$ alkyl, phenyl or alkoxy; and
when Y is $BR_aR_b$, then $R_a$ and $R_b$ form bidentate alkoxy; and
ii) a compound selected from the group consisting of $(R')_2Zn$, $(R')_2CuLi$, $(R')_2Cu(CN)Li_2$, $R'R''CuLi$ and $R'R''Cu(CN)Li_2$, wherein R' is a group of formula V with $R_1$ and $R_2$ having the same structures as defined above and R" is a heteroaryl group,

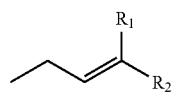

V in an inert solvent, and optionally in the presence of an adequate promoter to obtain a compound of formula VI;

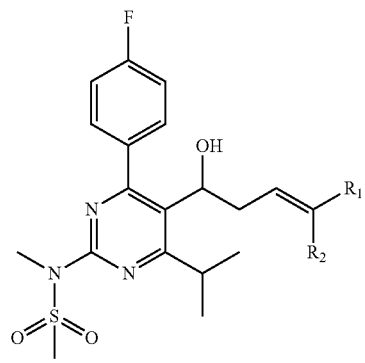

VI b) oxidative cleavage of the aliphatic carbon-carbon double bond of the obtained compound of formula VI and optionally isolating the intermediate of formula VII;

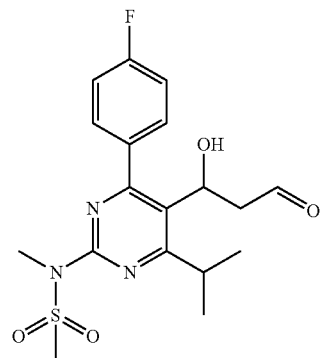

VII c) dehydration of intermediate of formula VII; and
d) isolation of compound of formula I.

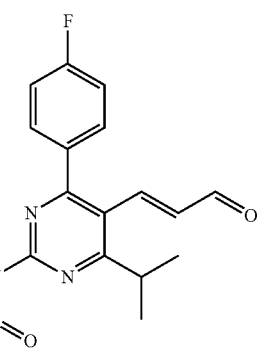

I

According to another embodiment of the present invention, a propenal intermediate of formula I obtained according to the process of the present invention is provided, which is used as an intermediate in the process for the preparation of Rosuvastatin or salts thereof.

According to another embodiment of the present invention, a compound of formula VI is provided, and a compound of formula VIa, which is N-(4-(4-fluorophenyl)-5-(1-hydroxy-but-3-enyl)-6-isopropylpyrimidin-2-yl)-N-methyl methanesulfonamide, and both compounds are used as intermediates in the process for the preparation of the propenal intermediate of formula I and Rosuvastatin or salts thereof.

According to another embodiment of the present invention, a compound of formula VII is provided, which is N-(4-(4-fluorophenyl)-5-(1-hydroxy-3-oxopropyl)-6-isopropylpyrimidin-2-yl)-N-methylmethanesulfonamide, and is used as an intermediate in the process for the preparation of the propenal intermediate of formula I and Rosuvastatin or salts thereof.

Preferred embodiments of the present invention are set out in dependent claims 2 to 13.

Other objects and advantages of the present invention will become apparent to those skilled in the art in view of the following detailed description.

DETAILED DESCRIPTION OF THE INVENTION

The present invention relates to an improved process for the preparation of compound of Formula (I) or derivates thereof in a stable form, which is characterized in substantially shorter reaction time, milder and safer reaction conditions, without sacrificing the yield and quality of the product and low cost of reactants and reagents.

According to the present invention, the process for the preparation of propenal intermediate of formula I or its derivatives comprises the following steps:

Step a) Preparation of Compound of Formula VI

The reaction of compound of formula III with an unsaturated compound of formula IV is carried out in an inert solvent such as THF, toluene, diethylether or other ethers. The preferred solvent is THF. The compound of formula IV is prepared shortly before use from the corresponding halide according to known prior art processes and is used directly and without further purification.

In one embodiment of the present invention, the preferred compound of formula IV is allylmagnesium bromide, which is prepared prior to use by dropwise treatment of activated magnesium turnings with an ethereal solution of allylbromide.

The molar ratio of compound of formula IV with respect to the compound of formula III is from 3:1 to 1.1:1, preferably from 2.5:1 to 1.5:1. The most preferred molar ratio of (compound of formula IV):(compound of formula III) is 2:1. The reaction temperature is from about −30 to 40° C., preferably from about −10 to 30° C., more preferably from about −5 to 5° C.

According to another embodiment of the present invention, the preferred compound of formula IV is selected from allyltri(alkyl)silane, allyltrichlorosilane or allyltri(alkyl)stannane, preferably allyltri(alkyl)silane. The preferred compound of formula IV in this aspect of the invention is allyltrmethylsilane.

A solution of compound of formula III in an inert solvent is treated with allyltrimethylsilane or allyltrichlorosilane in the presence of a promoter. The promoter is selected from a Lewis acid, such as boron trifluoride, titanium tetrachloride or titanium tetraisopropoxide, or a Lewis base, such as phosphoramide, formamide, sulfoxide, N-oxide, or a fluoride anion source, such as CsF, tetrabutylammonium fluoride. The preferred promoter is tetrabutylammonium fluoride.

The molar ratio of the promoter with respect to the compound of formula III is from 0.1:1 to 1.1:1, preferably from 0.3:1 to 0.7:1. The preferred molar ratio of (promoter):(compound of formula III) is 0.5:1. The temperature of the reaction is from about −10° C. to 40° C., preferably from about 0° C. to 30° C., more preferably from about 12° C. to 25° C.

According to another embodiment of the present invention, compound of formula VI is obtained by reacting compound of formula III with a compound selected from the group consisting of $(R')_2Zn$, $(R')_2CuLi$, $(R')_2Cu(CN)Li_2$, $R'R''CuLi$ and $R'R''Cu(CN)Li_2$, wherein R' is a group of formula V

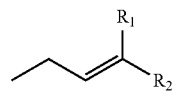

V wherein $R_1$ and $R_2$ is independently selected form H, alkyl, aryl or a heterocyclic moiety; and R" is a heteroaryl group.

According to another embodiment of the present invention, when $R_1$ and $R_2$ are both represent H in the structural formula VI, then compound of formula VIa is provided, which is N-(4-(4-fluorophenyl)-5-(1-hydroxybut-3-enyl)-6-isopropylpyrimidin-2-yl)-N-methylmethane-sulfonamide.

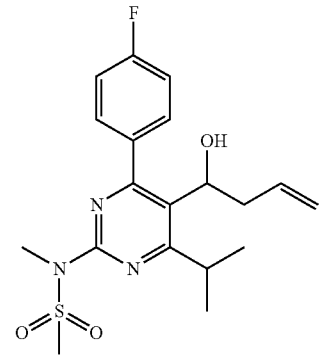

VIa

Step b): Oxidative Cleavage of the Alkene Functionality in Compounds of Formula VI The conversion of the aliphatic carbon-carbon double bond in compound of formula VI is carried out by oxidative cleavage, wherein the aliphatic carbon-carbon double bond is first oxygenated and the obtained intermediate is further cleaved to provide the aldehyde of formula VII. The oxygenation and the cleavage steps are conducted either concurrently or consecutively.

According to one embodiment of the present invention, the compound of formula VI is treated with $OsO_4$ in the presence of $NaIO_4$ in a suitable solvent mixture. Methanol, ethanol, water and buffer solution of pH value 6-8 (phosphoric or other salts) or a combination of them may be used as a solvent. Preferably, a mixture of methanol and water or a pH 7 buffer solution is used. The preferred solvent mixture is methanol and phosphoric salts buffer solution (pH 7). The volume ratio of the solvent mixture is from 1:1 to 20:1 (alcoholic part: aqueous part), preferably from 5:1 to 15:1, more preferably from 9:1 to 12:1.

A solution of OsO$_4$ of 4% wt. in water is used. However, as this reagent is considered toxic, the quantity employed has been limited to minimum requirements without compromising the efficiency of the reaction.

The weight to weight (w/w) ratio of OsO$_4$ with respect to the compound of formula VI is from 0.05:100 to 0.5:100, preferably from 0.1:100 to 0.4:100, more preferably 0.25:100.

The molar ratio of NaIO$_4$ with respect to the compound of formula VI is from 2:1 to 5:1, preferably from 2.5:1 to 4:1, more preferably 3:1.

The temperature of the reaction is from about −20° C. to 40° C., preferably from about −10° C. to 30° C., more preferably from about −5° C. to 20° C.

Alternatively, the oxidative cleavage is conducted by first treating the compound of formula III with OsO$_4$, Upon the completion of the oxidation, NaIO$_4$ is added to cleave the so-formed single bond.

According to another embodiment of the present invention, the oxidative cleavage is conducted by ozonolysis. Compound of formula VI is dissolved in methanol or dichloromethane and is subsequently treated with O$_3$, generated from an ANSEROS COM-CD-HF2 apparatus using a compressed air or oxygen gas tank. The preferred solvent is methanol. The temperature of the reaction is form about −30° C. to 80° C., preferably from about −10° C. to 25° C., most preferably from about 0° C. to 5° C.

The resulting ozonide intermediate is subjected to cleavage conditions. The cleavage of the ozonide intermediates leads to several products, such as alcohols, aldehydes, carboxylic acids, or derivatives thereof, depending on the reagent used. For example, alcohols are obtained when hydride donors such as LiAlH$_4$, NaBH$_4$, BH$_3$ are used. The use of oxidative reagents, such as oxygen, peroxyacids, hydrogen peroxide, produces carboxylic acids or their derivatives (esters, amides etc). The use of mild reductive reagents, such as triphenylphosphine, thiourea, zinc dust, or dimethyl sulfide, produces aldehydes or ketones.

Suitable conditions for cleavage of ozonide compound include the use of reagents that are able to convert the ozonide compound to the desired hydroxy-aldehyde intermediate of formula VII. Said aldehyde is obtained using a reagent selected from Zn/acetic acid, catalytic hydrogenation, triethylamine, trimethyl phosphite, thiourea, tri(alkyl)phosphines and tri(aryl)phosphines, for example trimethylphosphine, tributylphosphine and triphenylphosphine, di(alkyl)sulfides, such as dimethylsulfide, and di(alkyl)disulfides and di(aryl)disulfides, such as dimethyldisulfide and diphenyldisulfide. The preferred reagent for the cleavage of the ozonide compound is dimethylsulfide.

The molar ratio of dimethylsulfide with respect to the compound of formula V is form 1:1 to 7:1, preferably from 2:1 to 5:1, the most preferred (Me$_2$S):(compound of formula V) molar ratio is 2:1. The temperature of the reaction is form about −20 to 40° C., preferably from about −10 to 30° C., more preferably from about 10 to 20° C.

The crude reaction mixture that contain the hydroxy-aldehyde intermediate of formula VII is either subjected to an adequate workup, optionally followed by silica gel column purification, or further use without any treatment.

According to one embodiment of the present invention, the crude reaction mixture from the oxidative cleavage step is used as a starting material for the subsequent step without any treatment.

According to another embodiment of the present invention, the crude reaction mixture from the oxidative cleavage step is filtered through a celite bed followed by washing with methanol and the filtrate is used directly in the subsequent step.

According to yet another embodiment of the present invention, the crude reaction mixture from the oxidative cleavage step is subjected to bi-phasic solvent extraction workup followed by evaporating-off the solvent and the residue is used in the subsequent step. A portion of this residue is purified by column chromatography to afford pure hydroxy-aldehyde intermediate of formula VII.

According to another embodiment of the present invention, compound of formula VII is provided, which is N-(4-(4-fluorophenyl)-5-(1-hydroxy-3-oxopropyl)-6-isopropylpyrimidin-2-yl)-N-methylmethanesulfonamide.

Step c): Dehydration of the Hydroxy-Aldehyde (Compound of Formula VII)

Treatment of the hydroxy-aldehyde intermediate of formula VII with a base results in its dehydration under the influence of the neighboring carbonyl group, providing the desired conjugated aldehyde of formula I.

The use of inorganic bases at this stage is beneficial compared to organic ones due to the simplification of the isolation procedure of the final product. Inorganic bases used are selected from K$_2$CO$_3$, Na$_2$CO$_3$, NaOH, KOH, etc. The preferred inorganic base is K$_2$CO$_3$.

The reaction is carried out in low molecular weight alcohols, such as methanol, ethanol. The preferred solvent is methanol. The temperature of the reaction is from about −20° C. to 40° C., preferably from about −10° C. to 30° C., more preferably from about −5° C. to 20° C.

Step d): Isolation of Compound of Formula I

The crude reaction mixture resulting from the dehydration step is subjected to an acidic workup and pure conjugated aldehyde of formula I is obtained by recrystallization either after column purification or directly from the workup residue.

According to one embodiment of the present invention, the workup residue from the dehydration step is purified by silica gel column chromatography (10-30% AcOEt: cyclohexane) and recrystallized from 20% AcOEt:hexane at 0° C.

According to another embodiment of the present invention, pure compound of formula I is obtained by recrystallization (20% AcOEt:cyclohexane at 0° C.) directly from the workup residue obtained from the dehydration step.

The process of the present invention will be demonstrated in more details with reference to the following examples, which are provided by way of illustration only and should not be construed as limit to the scope of the reaction in any manner.

Example 1

Magnesium (13.8 g, 570 mmol) is charged into a 3-neck round-bottom flask and dried under heat and vacuum. Then the flask is purged with Argon. A solution of allylbromide (24.8 mL, 285 mmol) in 560 mL diethylether is added dropwise. The reaction mixture is stirred for 30 min after the completion of the addition. The reaction mixture is left to settle and the supernatant is added to a solution of N-[4-(4-fluorophenyl)-5-formyl-6-isopropylpyrimidin-2-yl]-N-methylmethanesulfonamide (40 g, 114 mmol) in 1120 mL THF at −5° C. to 5° C. under stirring. Reaction is monitored by TLC.

Upon completion of the reaction, 100 mL 1N HCl is charged into the reaction mass and stirred for 30 min. Layers are separated and the aqueous layer is extracted with 500 mL ethyl acetate twice. Organic layers are combined and washed with 100 mL DM water and 100 mL brine, subsequently. Organic layer is dried over 10 g of anhydrous Na$_2$SO$_4$. The solution is filtered and the filtrate is evaporated till dry. To the residue, 100 mL cyclohexane is added and the mass is stirred and filtered to obtain 36.5 g (81% yield) of N-[4-(4-fluorophenyl)-5-(1-hydroxybut-3-enyl)-6-isopropylpyrimidin-2-yl]-N-methylmethanesulfon-amide.

mp: 125.7-126.4° C.; LC-MS (CI) m/z: 394 (MO, 376, 316; IR (KBr) cm$^{-1}$: 3346, 3075, 3047, 2976, 2939, 2878, 1641, 1606, 1538, 1511, 1442, 1412, 1382, 1223, 1159, 1142.68, 1050, 961; $^1$H NMR (300 MHz, CDCl$_3$) δ 7.48 (m, 2H), 7.12 (m, 2H), 5.64 (m, 1H), 5.09 (d, J=12.2 Hz, 2H), 4.96 (dd, J=9.3, 4.7 Hz, 1H), 3.81 (m, 1H), 3.52 (s, 3H), 3.48 (s, 3H), 2.65 (m, 1H), 2.46 (m, 1H), 2.35 (bm, 1H), 1.35 (d, J=6.7 Hz, 6H), 1.30 (d, J=6.5 Hz, 6H); $^{13}$C NMR (75 MHz, CDCl$_3$) δ 177.6, 165.5, 164.8, 161.5, 157.2, 134.8, 134.7, 134.0, 131.0, 130.9, 124.3, 118.6, 115.4, 115.1, 68.7, 42.3, 41.8, 32.9, 32.4, 22.7, 22.1.

Example 2

A 50 mL round-bottom flask equipped with a stirring bar is dried under heat and vacuum followed by purged with Argon and charged with 1 g (2.85 mmol) of N-[4-(4-fluorophenyl)-5-formyl-6-isopropylpyrimidin-2-yl]-N-methylmethanesulfonamide and 28 mL of dry THF. The solution is cooled in an ice bath and 900 mg (2.85 mmol) solid TBAF.3H$_2$O are added in two equal portions in the space of 5 min. The reaction mixture is stirred at 0° C. for 1 hour and at 20° C.-25° C. for 12 hours. It is then treated with 10 mL aqueous 1N HCl and extracted with ethyl acetate (2×50 mL).

The organic layers are combined and washed with DM water (10 mL) and brine (10 mL) followed by drying over 500 mg of anhydrous Na$_2$SO$_4$. The mass is filtered and the filtrate is concentrated under vacuum. The residue is purified through silica gel column chromatography eluting with 30% ethylacetate:cyclohexane to provide 560 mg (50%) of the desired N-[4-(4-fluorophenyl)-5-(1-hydroxybut-3-enyl)-6-isopropylpyrimidin-2-yl]-N-methylmethanesulfonamide.

Example 3

To a solution of N-[4-(4-fluorophenyl)-5-(1-hydroxybut-3-enyl)-6-isopropyl-pyrimidin-2-yl]-N-methylmethanesulfonamide (2 g, 5.08 mmol) in a mixture of 30 mL methanol and 4 mL buffer solution (pH=7), sodium periodate (3.2 g, 15.2 mmol) and osmium tetroxide (0.3 mL, 4% wt. in water, 13 mg) are added at room temperature. The reaction mass is stirred and the progress of the reaction is monitored by TLC. Upon completion of the reaction, the reaction mixture is filtered through celite bed (1 g) and washed with ethyl acetate (2×10 mL). The filtrate is distilled under reduced pressure until solvents are removed. To the residue, ethyl acetate (200 mL) is added and washed with DM water (50 mL) and brine (50 mL), subsequently. The solvent is distilled off under reduced pressure to afford 2.1 g crude product. Part of the residue (200 mg) is purified through silica gel column chromatography eluting with (20%-30%) ethylacetate:cyclohexane to obtain 60 mg pure N-(4-(4-fluorophenyl)-5-(1-hydroxy-3-oxopropyl)-6-isopropylpyrimidin-2-yl)-N-methylmethanesulfonamide.

LC-MS (CI) m/z: 396 (MH$^+$), 378, 352, 274; IR (KBr) cm$^{-1}$: 3500, 2966, 2935, 2872, 1724, 1606, 1548, 1510, 1441, 1377, 1336, 1229, 1556, 963; $^1$H NMR (300 MHz, CDCl$_3$) δ 9.75 (s, 1H), 7.53 (m, 2H), 7.15 (m, 2H), 5.55 (dd, J=10.4, 2.6 Hz, 1H), 3.75 (m, 1H), 3.54 (s, 3H), 3.49 (s, 3H), 3.16 (dd, J=18.6, 10.4 Hz, 1H), 2.66 (dd, J=18.6, 2.5 Hz, 1H), 1.37 (d, J=6.8 Hz, 1H), 1.31 (d, J=6.5 Hz, 1H); $^{13}$C NMR (75 MHz, CDCl$_3$) δ 200.6, 177.7, 165.4, 164.9, 161.6, 157.3, 134.5, 134.4, 130.9, 130.8, 123.0, 115.5, 115.2, 63.8, 50.2, 42.3, 32.9, 32.3, 22.6, 21.9.

The remaining residue (1.9 g) is dissolved in 25 mL methanol. Potassium carbonate (1.4 g, 10.1 mmol) is added and the reaction mass is stirred at room temperature. The progress of the reaction is monitored by TLC. Upon completion of the reaction, HCl 1N (100 mL) is added. Methanol is distilled off under reduced pressure and the remaining aqueous solution is extracted with ethyl acetate (2×300 mL). Organic layers are combined and washed with DM water (50 mL) and brine (100 mL). The organic layer is distilled off under reduced pressure till dry.

The residue is purified by column chromatography eluting with (20%-30%) ethylacetate:cyclohexane and recrystallising from 20% ethylacetate:hexane at (0° C.-5° C.) to afford 330 mg (17%) of N-[4-(4-fluorophenyl)-6-isopropyl-5-(3-oxoprop-1-enyl)pyrimidin-2-yl]-N-methylmethanesulfonamide.

LC-MS (CI) m/z: 376 (M-H), 298; IR (KBr) cm$^{-1}$: 3423, 3073, 3015, 2971, 2933, 2872, 2727, 1693, 1603, 1547, 1509, 1445, 1378, 1331, 1224, 1155, 1127, 1066, 959; $^1$H NMR (300 MHz, CDCl$_3$) δ 9.61 (d, J=7.4 Hz, 1H), 7.59 (m, 2H), 7.53 (d, J=16.3 Hz, 2H), 7.14 (m, 2H), 6.20 (dd, J=16.3, 7.4 Hz, 1H), 3.60 (s, 3H), 3.51 (s, 3H), 3.39 (m, 1H), 1.33 (d, J=6.7 Hz, 9H); $^{13}$C NMR (75 MHz, CDCl$_3$) δ 192.5, 175.0, 165.3, 164.6, 162.0, 158.1, 146.9, 135.2, 133.5, 133.4, 131.9, 131.8, 118.3, 115.6, 115.4, 42.3, 32.9, 32.1, 21.7.

Example 4

To a solution of N-[4-(4-fluorophenyl)-5-(1-hydroxybut-3-enyl)-6-isopropyl-pyrimidin-2-yl]-N-methylmethanesulfonamide (5 g, 12.7 mmol) in a mixture of 64 ml methanol and 10 ml buffer solution (pH=7), sodium periodate (8.15 g, 38.1 mmol) and osmium tetraoxide (0.8 ml, 4% wt. in water, 34.6 mg) are added at room temperature. The reaction mass is stirred and the progress of the reaction is monitored by TLC. Upon completion of the reaction, the reaction mixture is filtered through 2 g celite bed and washed twice with 20 ml methanol.

Potassium carbonate (5.3 g, 38.1 mmol) is added to the filtrate at room temperature. Upon completion of the reaction, HCl 1N (150 mL) is added. Methanol is distilled off under reduced pressure and the aqueous residue is extracted ethyl acetate (2×400 mL). Organic layers are combined and washed with DM water (150 mL) and brine (200 mL). The organic solvent is distilled off under reduced pressure to give 4.5 g (94%) of N-[4-(4-fluorophenyl)-6-isopropyl-5-(3-oxoprop-1-enyl)pyrimidin-2-yl]-N-methylmethanesulfonamide.

The product is purified through silica gel column chromatography eluting with (20-30%) ethylacetate:cyclohexane and recrystallised from cyclohexane to give 1.76 g (40% yield) of N-[4-(4-fluorophenyl)-6-isopropyl-5-(3-oxoprop-1-enyl)pyrimidin-2-yl]-N-methylmethanesulfonamide.

Example 5

To a solution of N-[4-(4-fluorophenyl)-5-(1-hydroxybut-3-enyl)-6-isopropyl-pyrimidin-2-yl]-N-methylmethanesulfonamide (2 g, 5.08 mmol) in a mixture of 30 ml methanol and 4 ml buffer solution (pH=7), sodium periodate (3.2 g, 15.2 mmol) and osmium tetroxide (0.3 ml, 4% wt. in water, 13 mg) are added at room temperature. The reaction mass is stirred and the progress of the reaction is monitored by TLC. Upon completion of the reaction, potassium carbonate (2.1 g, 15.3 mmol) is added to the reaction mixture at room temperature. The progress of the reaction is monitored by TLC.

Upon completion of the reaction, HCl 1N (150 mL) is added to the reaction mass. Methanol is distilled off under reduced pressure and the aqueous residue is extracted with ethyl acetate (2×300 mL) Organic layers are combined and washed with DM water (150 mL) and brine (100 mL). The organic solvent is distilled off under reduced pressure to yield 1.8 g (94%) of N-(4-(4-fluorophenyl)-6-isopropyl-5-(3-oxoprop-1-enyl)pyrimidin-2-yl)-N-methylmethanesulfonamide.

Example 6

N-[4-(4-fluorophenyl)-5-(1-hydroxybut-3-enyl)-6-isopropyl-pyrimidin-2-yl]-N-methylmethanesulfonamide (4 g, 10.2 mmol) is diluted in 102 mL methanol. $O_3$ gas is bubbled through the solution at −15° C. to −10° C. for 60 min. Reaction solution is bubbled with Argon for 2 min to remove the excess of $O_3$. Dimethylsulfide (1.5 ml, 20.3 mmol) is added to the solution, maintaining stirring for 2 hours. Upon completion of the reaction, the solution is distilled under reduced pressure to remove the excess of dimethylsulfide and solvent. The residue is diluted in 200 mL dichloromethane, washed with DM water (50 mL), brine (50 mL) and dried over magnesium sulfate (1 g). The solvent is removed by distillation under reduced pressure to afford 4.1 g of N-[4-(4-fluorophenyl)-6-isopropyl-5-(3-oxoprop-1-enyl)pyrimidin-2-yl]-N-methylmethanesulfonamide.

The compound is diluted in 51 ml methanol and potassium carbonate (2.8 g, 20.3 mmol) is added to the solution under stirring. The progress of the reaction is monitored by TLC. Upon completion of the reaction, the mixture is filtered and solvent is distilled off under reduced pressure till dry. The residue is diluted in 500 ml ethyl acetate, washed with DM water (100 ml) and brine (100 ml) and dried over $Na_2SO_4$ (2 g).

The organic layer is distilled off completely under reduced pressure to give 3.6 g (94%) of (N-(4-(4-fluorophenyl)-6-isopropyl-5-(3-oxoprop-1-enyl)pyrimidin-2-yl)-N-methyl-methanesulfonamide. Recrystallizing the latter from 20% ethylacetate:cyclohexane at (0-5° C.), 2.6 g (72%) of N-(4-(4-fluorophenyl)-6-isopropyl-5-(3-oxoprop-1-enyl)pyrimidin-2-yl)-N-methylmethanesulfonamide is obtained as an oily white-yellow solid.

Example 7

N-[4-(4-fluorophenyl)-5-(1-hydroxybut-3-enyl)-6-isopropyl-pyrimidin-2-yl]-N-methylmethanesulfonamide (4 g, 10.2 mmol) is diluted in 102 mL methanol. $O_3$ gas is bubbled through the solution at −15° C. to −10° C. for 60 min. Reaction solution is bubbled through with Argon for 2 min to remove the excess of $O_3$. Dimethylsulfide (1.5 ml, 20.3 mmol) is added to the solution, maintaining stirring for 2 hours. To the reaction mixture, potassium carbonate (2.8 g, 20.3 mmol) is added at room temperature. The progress of the reaction is monitored by TLC. Upon completion of the reaction, 150 ml sodium bicarbonate (aq.) is added and methanol is distilled off under reduced pressure. The residue is extracted with ethyl acetate (2×300 mL) and washed with DM water (100 mL) and brine (150 mL). The organic solvent is distilled off under reduced pressure to give 3.7 g (95%) of N-(4-(4-fluorophenyl)-6-isopropyl-5-(3-oxoprop-1-enyl)pyrimidin-2-yl)-N-methyl-methanesulfonamide The product is recrystallized from 20% ethylacetate:cyclohexane at 0° C. to 5° C. to afford 2.4 g (67%) of N-(4-(4-fluorophenyl)-6-isopropyl-5-(3-oxoprop-1-enyl)pyrimidin-2-yl)-N-methyl-methanesulfonamide as an oily white-yellow solid.

The present invention describes an efficient process for the preparation of (E)-N-(4-(4-fluorophenyl)-6-isopropyl-5-(3-oxoprop-1-enyl)pyrimidin-2-yl)-N-methyl methanesulfonamide, which is a useful intermediate for the preparation of (3R,5S,E)-7-(4-(4-fluorophenyl)-6-isopropyl-2-(N-methyl methylsulfonamido)pyrimidin-5-yl)-3,5-dihydroxy hept-6-enoic acid, commonly known as Rosuvastatin.

According to the present invention, the process for the preparation of the propenal intermediate of formula I avoids the use of toxic substances or limits their use to not more than stoichiometric quantities, and employs mild conditions also in terms of convenient reaction temperature, without using either low or refluxing temperature. Remarkably, the process of the present invention may be concluded in less than 24 hours in high yield by using inexpensive reagents.

While the present invention has been described with respect to the particular embodiments, it will be apparent to those skilled in the art that various changes and modifications may be made in the invention without departing from the spirit and scope thereof, as defined in the appended claims.

The invention claimed is:
1. A process for the preparation of (E)-N-(4-(4-fluorophenyl)-6-isopropyl-5-(3-oxoprop-1-enyl)pyrimidin-2-yl)-N-methylmethanesulfonamide of formula I which comprises:

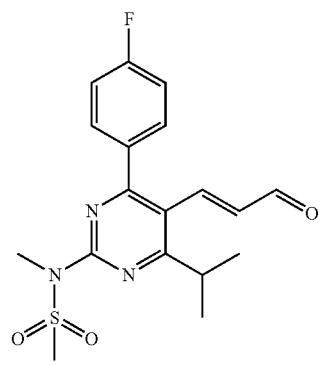

(a) Treating N-(4-(4-fluorophenyl)-5-formyl-6-isopropylpyrimidin-2-yl)-N-methyl methane-sulfonamide of formula III

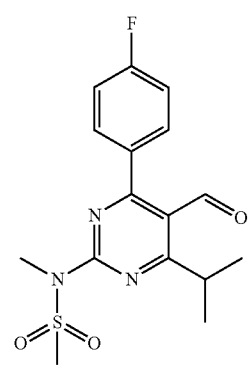

with a compound selected from
i) an unsaturated compound of formula IV

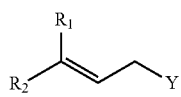

IV wherein $R_1$ and $R_2$ are independently selected from H, alkyl, aryl or a heterocyclic moiety;

Y is selected from M, MX, $BR_aR_b$ and $MR_aR_bRc$, wherein M is selected from alkali, Zn, Mg, Sn and Si;

X is selected from Cl, Br and I;

$R_a$, $R_b$ and $R_c$ are independently selected from X, H, $C_1$-$C_2$ alkyl, phenyl and alkoxy; and when Y is $BR_aR_b$, then $R_a$ and $R_b$ form bidentate alkoxy; and ii) a compound selected from $(R')_2Zn$, $(R')_2CuLi$, $(R')_2Cu(CN)Li_2$, $R'R''CuLi$ or $R'R''Cu(CN)Li_2$, wherein R' is a group of formula V with $R_1$ and $R_2$ having the same structures as defined above, and R'' is a heteroaryl group,

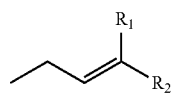

V in an inert solvent, optionally in the presence of a promoter, to obtain compound of formula VI:

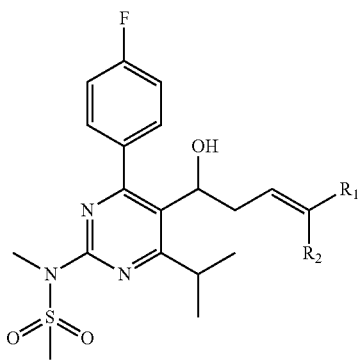

VI (b) oxidative cleavage of the aliphatic carbon-carbon double bond of the obtained compound of formula VI and optionally isolating intermediate of formula VII;

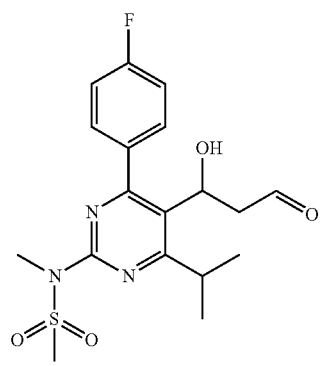

VII (c) dehydration of intermediate of formula VII; and (d) isolation of compound of formula I.

2. The process according to claim 1, wherein Y is MgX.

3. The process according to claim 1, wherein Y is $SiMe_3$ or $SiCl_3$.

4. The process according to claim 1, wherein step a) is carried out in the presence of a promoter, said promoter is either a Lewis acid selected from the group consisting of boron trifluoride, titanium tetrachloride or titanium tetraisopropoxide;

or said promoter is a Lewis base selected from the group consisting of phosphoramide, formamide, sulfoxide, N-oxide compounds, dimethyl formamide;

or said promoter is a fluoride anion source selected from the group consisting of CsF, tetrabutylammonium fluoride.

5. The process according to claim 1, wherein the oxidative cleavage is carried out by treating a compound of formula VI with $OsO_4$ and $NaIO_4$ simultaneously or in a stepwise manner.

6. The process according to claim 1, wherein the oxidative cleavage is carried out by treating a compound of formula VI with ozone ($O_3$) followed by cleavage of the ozonide compound.

7. The process according to claim 6, wherein the reagent used for cleavage of the ozonide compound is selected from Zn/acetic acid, dialkylsulfides and phosphines.

8. The process according to claim 1, wherein step c) is carried out by adding an inorganic base into a solution containing compound of formula VII.

9. The process according to claim 8, wherein the inorganic base is NaOH, KOH, $Na_2CO_3$, $K_2CO_3$.

10. The process according to claim 1, wherein the inert solvent of step a) is selected from tetrahydrofuran, toluene, diethylether or other ethers.

11. The process according to claim 1, wherein $R_1$ and $R_2$ both represent H.

12. A compound of formula VI, wherein $R_1$ and $R_2$ are independently selected from H, alkyl, aryl or a heterocyclic moiety

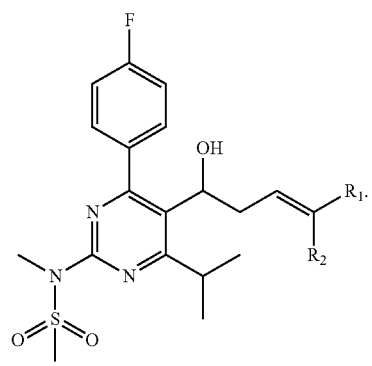

VI

13. A compound of formula VIa, which is N-(4-(4-fluorophenyl)-5-(1-hydroxybut-3-enyl)-6-isopropylpyrimidin-2-yl)-N-methyl methane-sulfonamide
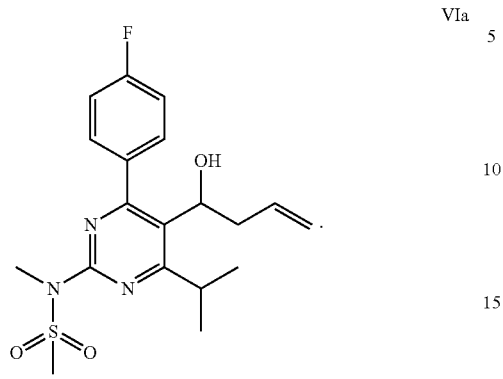
VIa
14. A compound of formula VII, which is N-(4-(4-fluorophenyl)-5-(1-hydroxy-3-oxopropyl)-6-isopropylpyrimidin-2-yl)-N-methylmethanesulfonamide.
15. The process according to claim 7, wherein the dialkylsulfide is $Me_2S$.
* * * * *